(12) United States Patent
Sawa

(10) Patent No.: US 7,081,101 B1
(45) Date of Patent: Jul. 25, 2006

(54) SHOULDER BRACE WITH BODY TO ARM ATTACHMENT STRAPS

(76) Inventor: Thomas M. Sawa, 2087 Oundas St. East, Suite 102, Mississauga, Ontario (CA) L4X 1M2

( * ) Notice: Subject to any disclaimer, the term of this patent is extended or adjusted under 35 U.S.C. 154(b) by 0 days.

(21) Appl. No.: 11/042,122

(22) Filed: Jan. 26, 2005

(51) Int. Cl.
*A61F 5/00* (2006.01)

(52) U.S. Cl. .......................................... 602/19; 602/20

(58) Field of Classification Search ................... 602/19, 602/20, 5; 128/869
See application file for complete search history.

(56) References Cited

U.S. PATENT DOCUMENTS

| | | | | |
|---|---|---|---|---|
| 4,735,198 A | * | 4/1988 | Sawa | 128/878 |
| 4,947,870 A | * | 8/1990 | Larcher | 128/875 |
| 5,188,587 A | * | 2/1993 | McGuire et al. | 602/20 |
| 5,628,725 A | * | 5/1997 | Ostergard | 602/62 |
| 6,106,493 A | * | 8/2000 | Rozell | 602/20 |
| 6,132,393 A | * | 10/2000 | Lundberg | 602/19 |
| 6,306,111 B1 | * | 10/2001 | Dean | 602/20 |
| 6,398,746 B1 | * | 6/2002 | Bramlage et al. | 602/5 |
| 6,709,411 B1 | * | 3/2004 | Olinger | 602/4 |
| 2002/0010409 A1 | * | 1/2002 | Bramlage et al. | 602/19 |

\* cited by examiner

*Primary Examiner*—Henry Bennett
*Assistant Examiner*—Dinnatia Doster-Greene

(57) ABSTRACT

A shoulder complex and upper arm injury reduction system having a torso fitting part, an upper arm wrap part, and at least one movement control strap constructed of non-stretchable material. The movement control straps are strategically anchored on the system to control posterior, anterior, and multidirectional movement of the upper arm wrap part relative to the torso fitting part. The straps are length adjustable to control the amount of movement of the upper arm wrap part relative to the torso fitting part, and prevent separation of the upper arm wrap part from the torso fitting part beyond the strap length. The system includes a control strap that extends from the shoulder capping region to a strap mounting location below or above the shoulder capping region. The strap is length adjustable to allow tension to be placed on the strap and to produce traction between the shoulder strapping region and the strap mounting location.

11 Claims, 13 Drawing Sheets

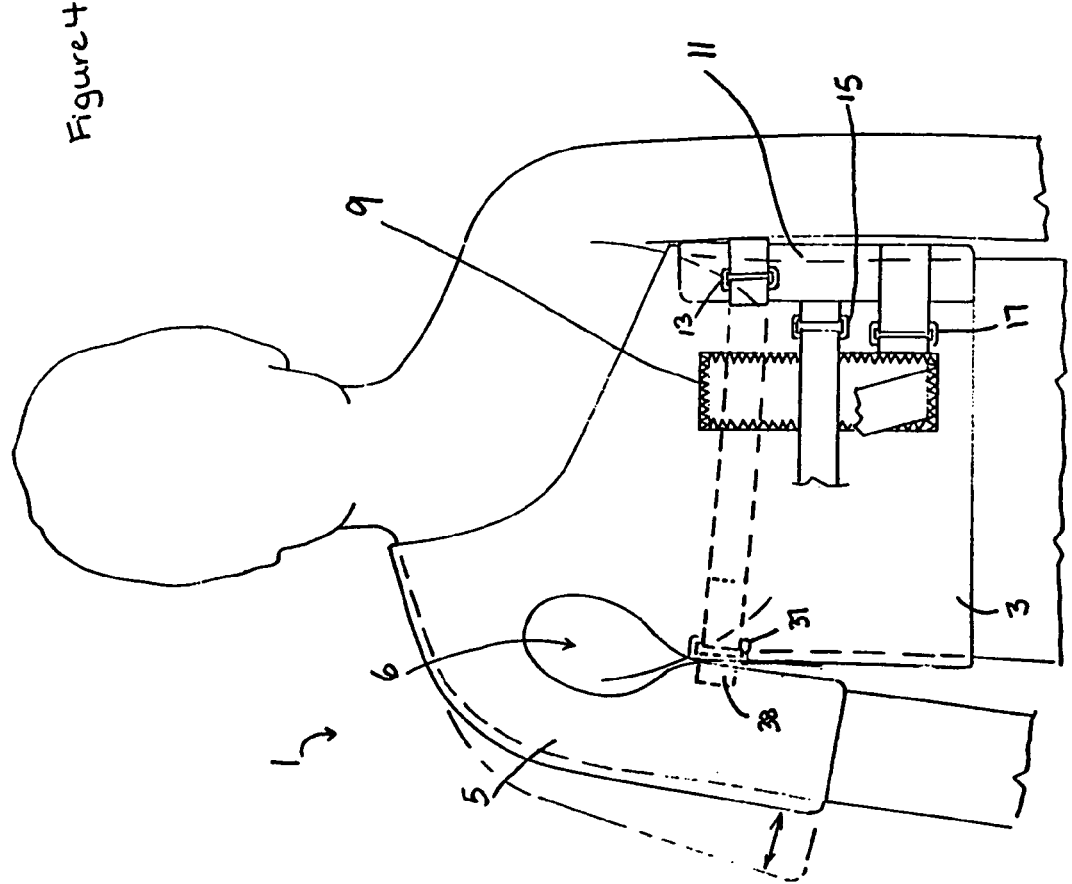
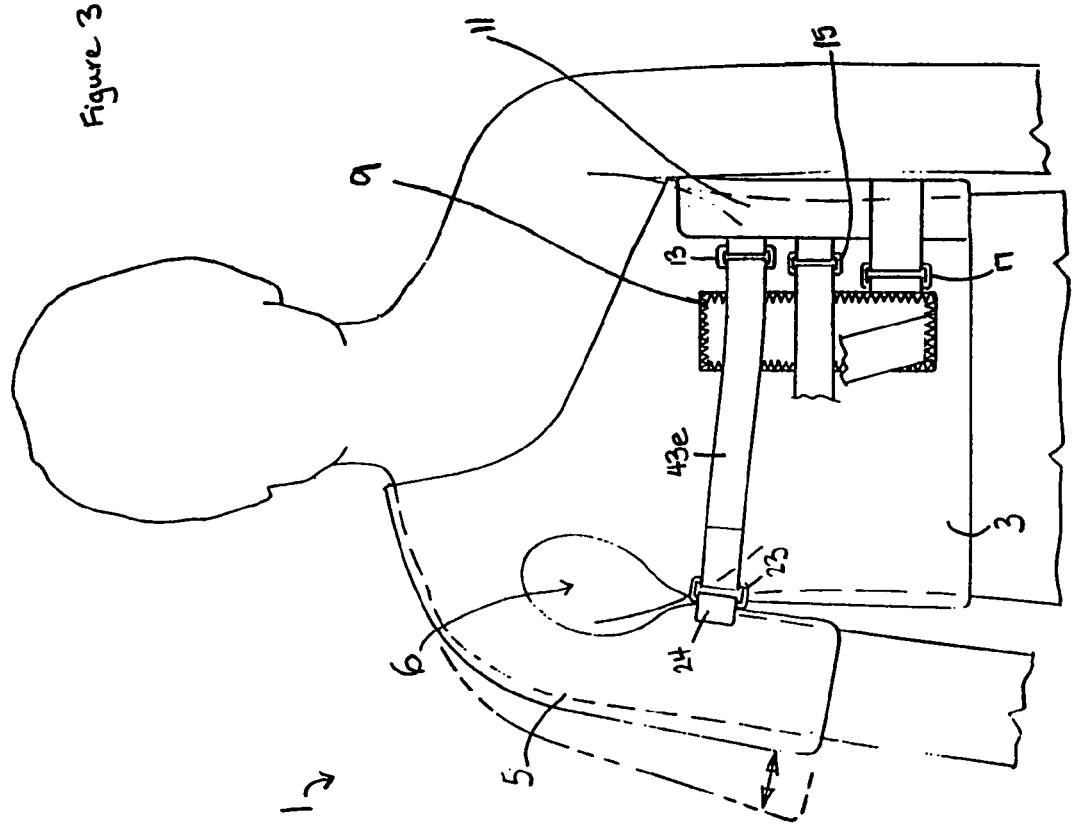

27;
SHOULDER BRACE WITH BODY TO ARM ATTACHMENT STRAPS

FIELD OF THE INVENTION

The present invention relates to a shoulder complex and upper arm injury reduction system. The system is particularly useful for athletes in contact sports.

BACKGROUND OF THE INVENTION

Dating back to 1988, I patented an injury reduction and stabilizing harness as described in my U.S. Pat. No. 4,735,198. According to my earlier patent, I used elastic straps on a torso and upper arm fitting harness to control the amount of movement of the upper arm relative to the torso of the user. The straps, according to my earlier patent, attached at their opposite ends by Velcro™ to different part of the harness.

My earlier patented harness allowed athletes or even people under general rehabilitation continued controlled use of an injured shoulder or upper arm. The elasticity of the straps, particularly once the straps are stretched, would slow movement of the injured body part rather than allowing the body part completely unrestricted free motion.

Since the time of my earlier patent, many athletes in professional sports have grown much bigger and much stronger. Consider the size of a lineman on a pro football team who will easily weight in excess of 300 pounds. Today's professional hockey players usually weight in excess of 200 pounds which is probably some 20 to 30 pounds heavier than the players in the 1980s. It is well accepted that athletes of the $21^{st}$ century are much larger, stronger and faster than their counterparts of the 1980s. As such, the harness as described in my 1988 patent, although providing extremely beneficial results at the time, is not capable of standing up to the tremendous physical punishment encountered by the larger athletes of the present.

SUMMARY OF THE INVENTION

The present invention provides a shoulder complex and upper arm injury reduction system. The system of the present invention comprises a torso fitting part, an upper arm wrap part and at least one movement control strap.

That strap has a first strap region which is secured by an anchor fixed at the torso fitting part and a second strap region which is anchored at the upper arm wrap part.

The strap itself is adjustable to different strap lengths between the first and second strap regions. The length to which the strap is adjusted sets the amount of movement of the upper arm wrap part relative to the torso fitting part. The strap is made from an essentially inelastic material such that the strap prevents separation of the upper arm wrap part from the torso fitting part beyond the strap length to which the strap is adjusted.

According to another aspect of the present invention, the torso fitting part includes a shoulder capping region and a control strap which extends from the shoulder capping region to a strap mounting location below the shoulder capping region. Alternatively, the strap can extend from a location below the shoulder capping region to a strap mounting location above the shoulder capping region. The strap is length adjustable to allow tension to be placed on the strap and to produce traction within the system between the shoulder strapping region and the strap mounting location.

The key to the present invention lies in the use of length adjustable, essentially non-stretch straps, which can be fixedly anchored in position on the system. Through the use of these three features, the straps, while allowing a controlled limited movement of the upper arm wrap part relative to the torso fitting part, are strong enough to control even the biggest and strongest athlete from moving beyond a desired range of motion set by the control straps.

BRIEF DESCRIPTION OF THE DRAWINGS

The above as well as other advantages and features of the present invention will be described in greater detail according to the preferred embodiments of the present invention, wherein:

FIGS. 3 and 4 are front views of the system of FIG. 1 with FIG. 3 showing positioning of a plurality of control straps to the front of the system while FIG. 4 shows positioning of one of those control straps to the rear of the system;

DETAILED DESCRIPTION ACCORDING TO THE PREFERRED EMBODIMENTS OF THE PRESENT INVENTION

Figure 1:
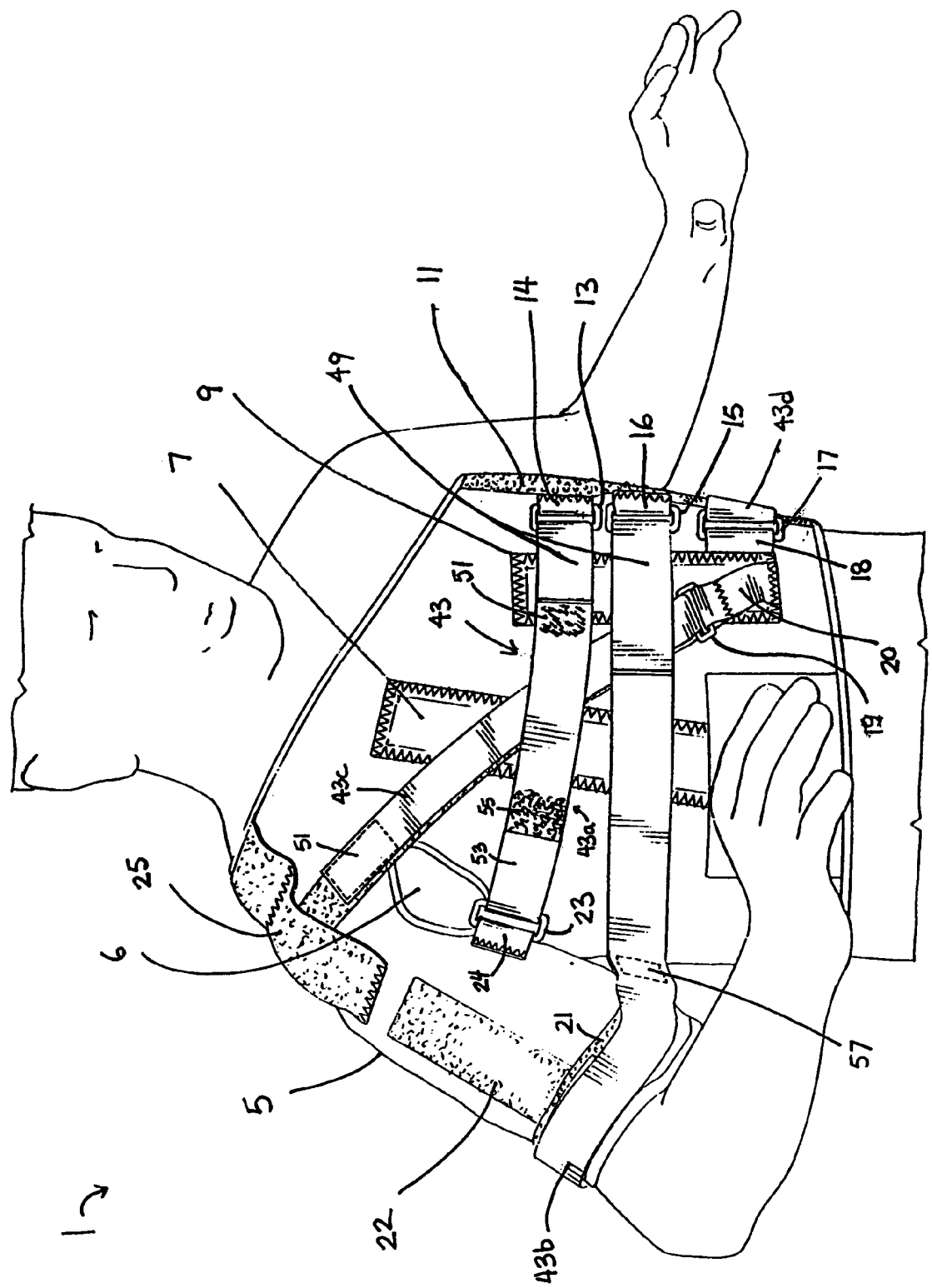
FIG. 1 is a front perspective view looking down on a shoulder complex and upper arm injury reduction system according to a preferred embodiment of the present invention.

FIG. 1 shows a shoulder complex and upper arm injury reduction system generally indicated at 1. This system is based on a corset like member comprising a torso fitting part 3 and an upper arm wrap part 5. The torso fitting part 3 and the upper arm wrap part 5, in the embodiment shown in FIG.

1, are part of a one piece corset provided with an underarm cutout 6. This underarm cutout allows movement of the upper arm wrap part 5 relative to the torso fitting part 3 without chaffing in the underarm region.

Torso fitting part 3 includes a side closure 11 which allows the entire corset to be opened for fitting on to the user including the fitting of the upper arm through part 5. Side closure 11, which is preferably a Velcro™ closure, can then be secured to hold the overall corset tightly wrapped on the body of the user.

Upper arm wrap part 5 preferably includes a side closure which allows the entire upper arm wrap part to be opened for fitting on to the arm of the user. The side closure, which is preferably a Velcro™ closure, can then be secured to hold the upper arm wrap tightly wrapped on the arm of the user. The side closure also allows different arm sizes to be accommodated.

Both the torso fitting part 3 and the upper arm wrap part 5 are preferably made from a rubbery stretch material such as neoprene or the like. This type of material is light in weight, hugs neatly to the user, and provides body warmth which is particularly useful if the system is being used with a previously injured body part. Even if there is no previous injury, the warmth, i.e. blood flow, induced by the neoprene or similar material helps to prevent an injury to the user. In addition, it can be appreciated that a stretchy blended cotton material or stretchy blended synthetic material, which is breathable, flexible and strong, can also be used for the torso fitting part 3 and the upper arm wrap part 5. However, this is not limiting and other materials are considered within the scope of the invention.

Figure 2:
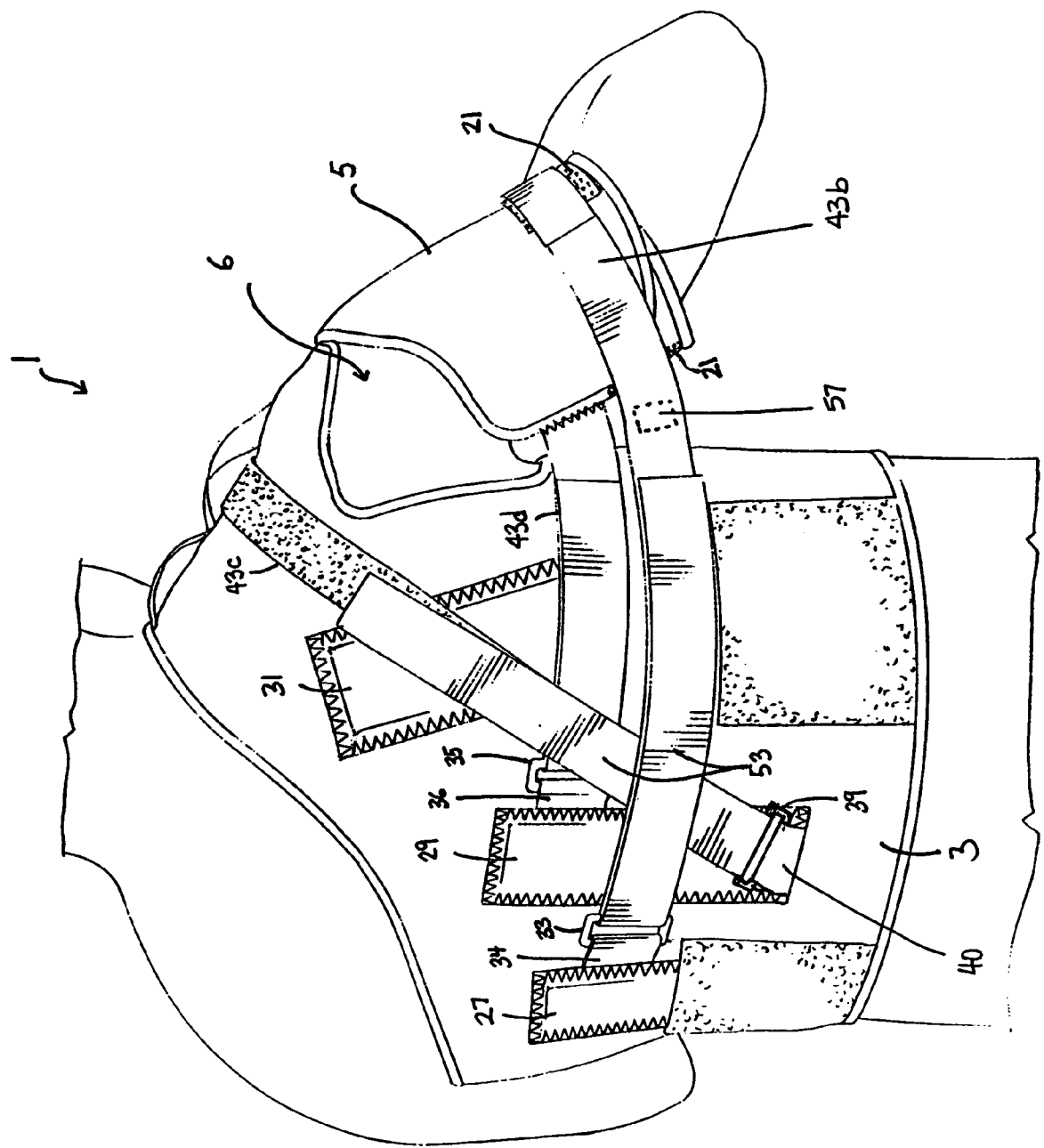
FIG. 2 is a rear perspective view of a system similar to that shown in FIG. 1 but set up in a different manner from that shown in FIG. 1.

A certain amount of stability is desired in the torso fitting part 3 so that it does not overstretch and move around while fitted to the user. To this end, flexible stabilizer bars 7 and 9 are secured, as by stitching for example, to the stretch material of the torso fitting part 3. FIG. 2 of the drawings shows 20 that further flexible stabilizer bars 27, 29 and 31 are provided on the rear surface of the torso fitting part 3.

The system described thus far is similar to what was disclosed in U.S. Pat. No. 4,735,198. However, substantial differences between the two systems as provided in the present invention will now be further described.

Torso fitting part 3 is provided with a series of rigid buckles 13, 15 and 17. These buckles are held in place by small non-stretchable anchoring straps 14, 16 and 18 respectively. A further buckle 19 is secured by anchoring strap 20 to the front side of the torso fitting part 3. The inclusion of the anchoring straps, which are permanently fastened to the torso fitting part 3, allow the buckles some freedom of movement outwardly away from the torso fitting part 3. This in turn allows for easy fitting of control straps, to be described later in detail, to be fitted through the buckles. Preferably, the anchoring straps 14, 16, 18, and 20 are permanently fastened to a location on the stabilizer bar 9 to provide greater stability and strength to the system.

In one preferred embodiment of the invention, provided on the upper arm wrap part 5 is a further rigid buckle 23 anchored or held fast on the upper arm wrap part 5 by a non-stretchable anchoring strap 24. Once again, the purpose of anchoring strap 24 is simply to remove buckle 23 far enough away from the surface of the upper arm wrap part 5 to accommodate the fitting of a control strap through the buckle.

Now turning to FIG. 2, further rigid buckles 33 and 35, which are secured by non-stretchable anchoring straps 34 and 36 respectively, are provided to the backside of the torso fitting part 3. A further rigid buckle 39, which is secured by non-stretchable anchoring strap 40, is provided on the backside of torso fitting part 3, as shown in FIG. 2. The inclusion of the anchoring straps, which are permanently fastened to the torso fitting part 3, allow the buckles some freedom of movement outwardly away from the torso fitting part 3. This in turn allows easy fitting of control straps, to be described later in detail, to be fitted through the buckles. Preferably, the anchoring straps 34, 36, and 40 are permanently fastened to locations on the stabilizer bar to provide greater stability and strength to the system.

In one embodiment of the invention, a further rigid buckle 37, which is secured by non-stretchable anchoring strap 38, is provided on the backside of torso fitting part 3, as shown in FIG. 4. Once again, the purpose of anchoring strap 38 is simply to remove buckle 37 far enough away from the surface of the upper arm wrap part 5 to accommodate the fitting of a control strap through the buckle.

Preferably anchoring straps 14, 16, 18, 20, 24, 34, 36, 38, and 40 are made from a material such as a woven nylon which is essentially stretch free. Such a material is also resistant to deterioration which might otherwise be caused by body sweat over the life of the system.

One of the keys to the present invention resides in the essentially immoveable location of the buckles on the system and the use of non-elastic, i.e. essentially stretch free, control straps, to be described later in detail, for controlling movement of the upper arm wrap part 5 relative to the torso fitting part 3 of the system 1.

Provided on upper arm wrap part 5 is an elongated Velcro™ surface member 21. This Velcro™ member 21 encircles most, if not all, of the outside surface of the upper arm wrap part 5 near its lower end as shown in FIGS. 1 and 2.

Further provided on upper arm wrap part 5 is a second Velcro™ surface member 22, which extends upwardly along the length of upper arm wrap part 5. Located directly over the shoulder capping region of upper arm wrap part 5 is a strap trapping loop 25.

To control movement of the upper arm wrap part 5 relative to the torso fitting part 3 of the system 1, at least one movement control strap 43 is provided. The control strap 43 is preferably made from an inelastic non-stretch material, such as woven nylon, and is anchored to the upper arm wrap part 5 and to the torso fitting part 3 such that the control strap 43 restricts and controls the amount and degree of posterior and anterior movement of the upper arm wrap part 5 from the torso fitting part 3 beyond the length of the strap, which length is adjustable as described later in detail, and to restrict and control multidirectional movements of the upper arm wrap part 5 from the torso fitting part 3 beyond the length of the strap, which length is adjustable as described later in detail.

In a preferred embodiment of the invention, the system 1 utilizes a series of control straps as illustrated in FIGS. 1 and 2. In this preferred arrangement, the control straps 43a, 43b, 43c, and 43d are of varying lengths, wherein each control strap has a first strap end region 45 and a second strap end region 47, which anchors to the torso fitting part 3 and the upper arm fitting part 5, as described later in detail.

Control strap 43a restricts the rearward movement of the upper arm wrap part 5 relative to the torso fitting part 3, and thus provides the capability of preventing movement of the shoulder joint into a position in which it could dislocate. In one aspect of the invention, the first strap end region 45 of control strap 43a is threaded through buckle 13, and is folded back over buckle 13 to form a first loop part 49. The first loop part 49 includes an interlocking Velcro™ surface region 51 to secure the first strap end region 45 to buckle 13. The second strap end region 47 of control strap 43*a* is threaded through buckle 23, and is folded back over buckle 23 to form a second loop part 53. The second loop part 53 includes an interlocking Velcro™ surface region 55 to secure the second strap end region to buckle 23. By adjusting the first loop part 49 and the second loop part 53, different strap lengths, which correspond to different ranges of movement, can be utilized.

Similarly, control strap 43*d* provides the capability of restricting the forward movement of the upper arm wrap 5 relative to the torso fitting part 3. In one aspect of the invention as illustrated in FIG. 2, the first strap end region 45 of control strap 43*d* is threaded through buckle 35, and is folded back over buckle 35 to form a first loop part 49. The first loop part 49 includes an interlocking Velcro™ surface region 51 to secure the first strap end region 45 to buckle 35. The second strap end region 47 of control strap 43*d* is threaded through buckle 37, and is folded back over buckle 37 to form a second loop part 53. The second loop part 53 includes an interlocking Velcro™ surface region 55 to secure the second strap end region 47 to buckle 37. By adjusting the first loop part 49 and the second loop part 53, different strap lengths, which correspond to different ranges of movement, can be utilized.

In an alternate embodiment, one of either the first strap end region 45 or the second strap end region 47 of control straps 43*a* and 43*d* is permanently attached to the torso fitting part 3 or the upper arm wrap part 5 respectively. Adjustments to the length of the control strap are made at the unfixed strap end region, which is threaded through a buckle and folded back over the buckle to form a loop part and secured using interlocking Velcro™ surface regions as described above. For example, as illustrated in FIG. 2, the second strap end region 47 of control strap 43*d* is permanently secured to the upper arm wrap part 5, and adjustment of the length of the control strap is made by adjusting the first loop part 49 of the first strap end region 45.

Figure 8:
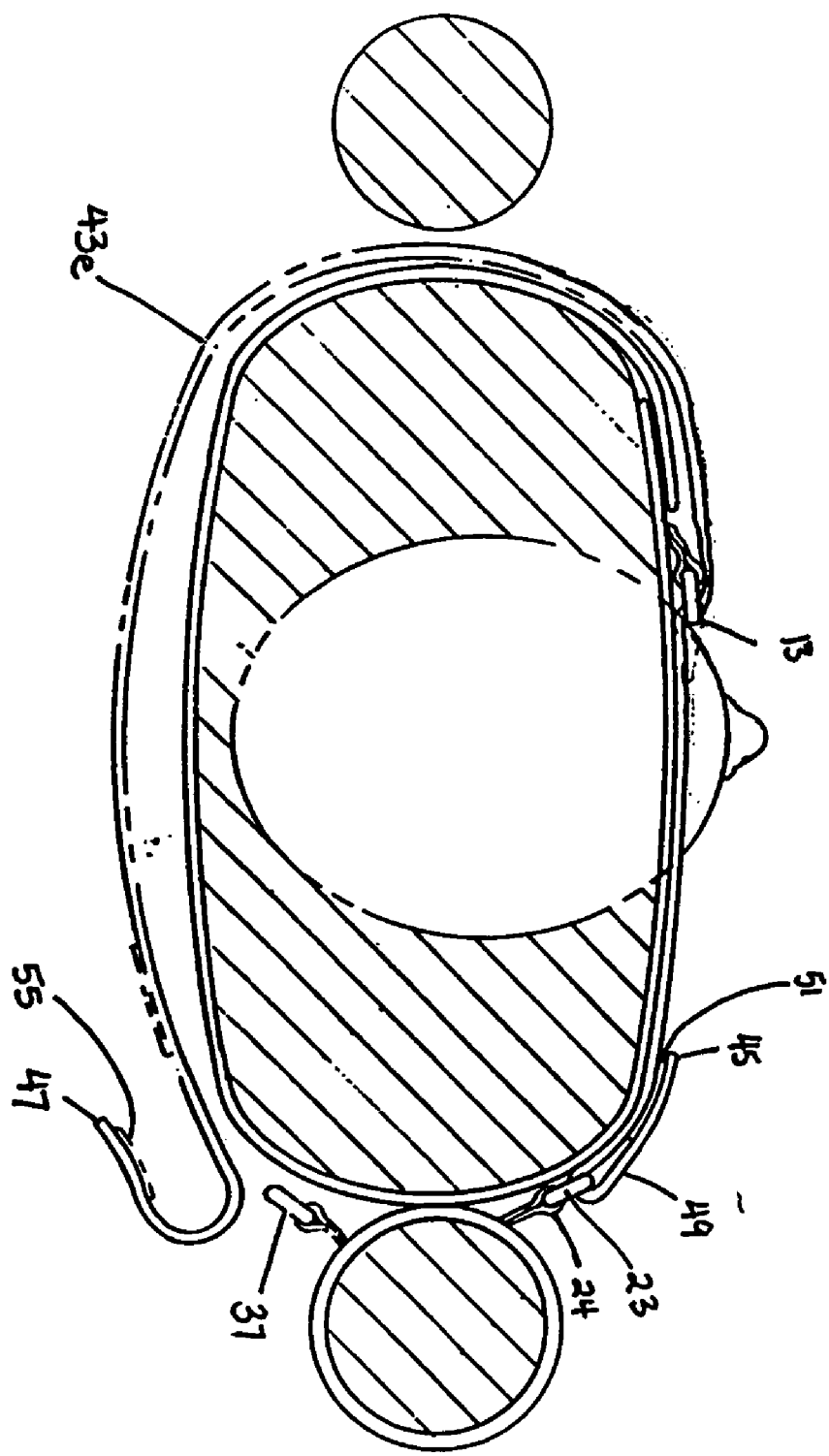
FIG. 8 is a top view looking down on the system of the present invention showing the position for an alternate control strap within the system.

In a further alternate embodiment as illustrated in FIGS. 3, 4, and 8, forward and rearward movement of the upper arm wrap part 5 is controlled by a single control strap 43*e*. In this embodiment, the first strap end region 45 of control strap 43*e* is threaded through buckle 23, and is folded back over buckle 23 to form a first loop part 49. The first loop part 49 includes an interlocking Velcro™ surface region 51 to secure the first strap region 45 to buckle 23. The second strap end region 47 of control strap 43*e* is threaded through buckle 37, and is folded back over buckle 37 to form a second loop part 53. The second loop part 53 includes an interlocking Velcro™ surface region 55 to secure the second strap region 47 to buckle 37. Control strap 43*e* is positioned to encircle the torso, and is threaded through buckle 13 to prevent slippage of the encircling position of control strap 43*e*. By adjusting the first loop part 49 and the second loop part 53, different strap lengths, which correspond to different ranges of movements, is achieved.

Control straps 43*a*, 43*d*, and 43*e* are designed to restrict the forward and rearward movement of the upper arm wrap part 5, and thereby restricting the forward and rearward movement of the shoulder joint and preventing the shoulder joint from moving into a position in which it could dislocate.

Control strap 43*b* controls the multidirectional movement of the upper arm wrap part 5 relative to the torso fitting part 3. In a preferred embodiment, control strap 43*b* is of an extended length wherein the first strap end region 45 is anchored at the front side of the torso fitting part 3, and the second strap end region 47 is anchored at the rear side of the torso fitting part 5. As illustrated in FIGS. 1 and 2, control strap 43*b* is positioned to encircle both the torso fitting part 3 and the upper arm wrap part 5, wherein a segment of control strap 43*b* is secured to Velcro™ member 21. In addition, control strap 43*b* is permanently affixed together, preferably by stitching, at a location 57 between the torso fitting part 3 and the upper arm wrap part 5.

The first strap end region 45 of control strap 43*b* is threaded through buckle 15, and is folded back over buckle 15 to form a first loop part 49. The first loop part 49 includes an interlocking Velcro™ surface region 51 to secure the first strap end region 45 to buckle 15. The second strap region 47 of control strap 43*b* is threaded through buckle 33, and is folded back over buckle 43 to form a second loop part 53. The second loop part 53 includes an interlocking Velcro™ surface region 55 to secure the second strap end region 47 to buckle 33. By adjusting the first loop part 49 and the second loop part 53, different strap lengths for control strap 43*b* is achieved. In particular, the stitching at location 57 allows for independent adjustment of the front portion of control strap 43*b*, located on the front side of the torso fitting part 3, and of the rear portion of control strap 43*b*, located on the rear side of the torso fitting part 3. Thus, this preferred arrangement of control strap 43*b* controls the multidirectional movement of the arm, including flexion and extension of the arm, internal and external rotation of the arm, and all combinations thereof. This is particularly useful for shoulders that are unstable in all directions of movement. Furthermore, stitching at location 57 also prevents control strap 43*b* from tangling and catching.

In an alternate embodiment of the invention [not shown], control strap 43*b* is preferably comprised of two identical straps 43*bb* and 43*bbb*, wherein control strap 43*bb* is positioned on the front side of torso fitting part 3 and control strap 43*bbb* is positioned on the rear side of torso fitting part 3. The first strap end region 45 of control strap 43*bb* is threaded through buckle 15, and is folded back over buckle 15 to form a first loop part 49. The first loop part 49 includes an interlocking Velcro™ surface region 51 to secure the first strap end region 45 to buckle 15. The second strap end region 47 of control strap 43*b*, which includes an interlocking Velcro™ surface region 55, is wrapped around and secured to Velcro™ member 21. The first strap end region 45 of control strap 43*bbb* is threaded through buckle 33, and is folded back over buckle 33 to form a first loop part 49. The first loop part 49 includes an interlocking Velcro™ surface region 51 to secure the first strap end region 45 to buckle 33. The second strap end region 47 of control strap 43*bbb*, which includes an interlocking Velcro™ surface region 55, is wrapped around and secured to Velcro™ member 21. Control straps 43*bb* and 43*bbb* are permanently affixed together, preferably by stitching, at a location 57 between the torso fitting part 3 and the upper arm wrap part 5. This alternate embodiment of control strap 43*b* allows different arm sizes to be accommodated.

Control strap 43*c* provides tension to the acromioclavicular (A/C) joint when there is interruption of the acromioclavicular ligaments, i.e. the conoid and trapezoid, and the coracoacromial ligaments. The degree of sprain or tear can vary from 0% to 100% disruption of these ligaments. Control strap 43*c* is positioned over the acromioclavicular joint to provide a splint-like application to provide stability while the acromioclavicular joint heals. Furthermore, the action of the control strap 43*c* will help to reduce pain, minimize soft tissue scarring and help promote a normal range of motion. Control strap 43*c* is anchored from a point on the front side of the torso fitting part 3, and extends over the shoulder capping region through strap trapping loop 25, and anchored to the rear side of the torso fitting part 3. In a preferred embodiment as illustrated in FIGS. 1 and 2, the first strap end region 45 of control strap 43c is threaded through buckle 19, and is folded back over buckle 19 to form a first loop part 49. The first loop part 49 includes an interlocking Velcro™ surface region 51 to secure the first strap end region 45 to buckle 19.

The second strap end region 47 of control strap 43c is threaded through buckle 39, and is folded back over buckle 39 to form a second loop part 53. The second loop part 53 includes an interlocking Velcro™ surface region 55 to secure the second strap end region 47 to buckle 39. Strap trapping loop 25 maintains the positioning of the control strap 43c, and prevents slippage of the control strap 43c.

In an alternate embodiment of the invention, one of either the first strap end region 45 or the second strap end region 47 of control strap 43c is anchored directly to the torso fitting part 3, and preferably affixed together with a stabilizer bar on the torso fitting part 3.

Figure 11:
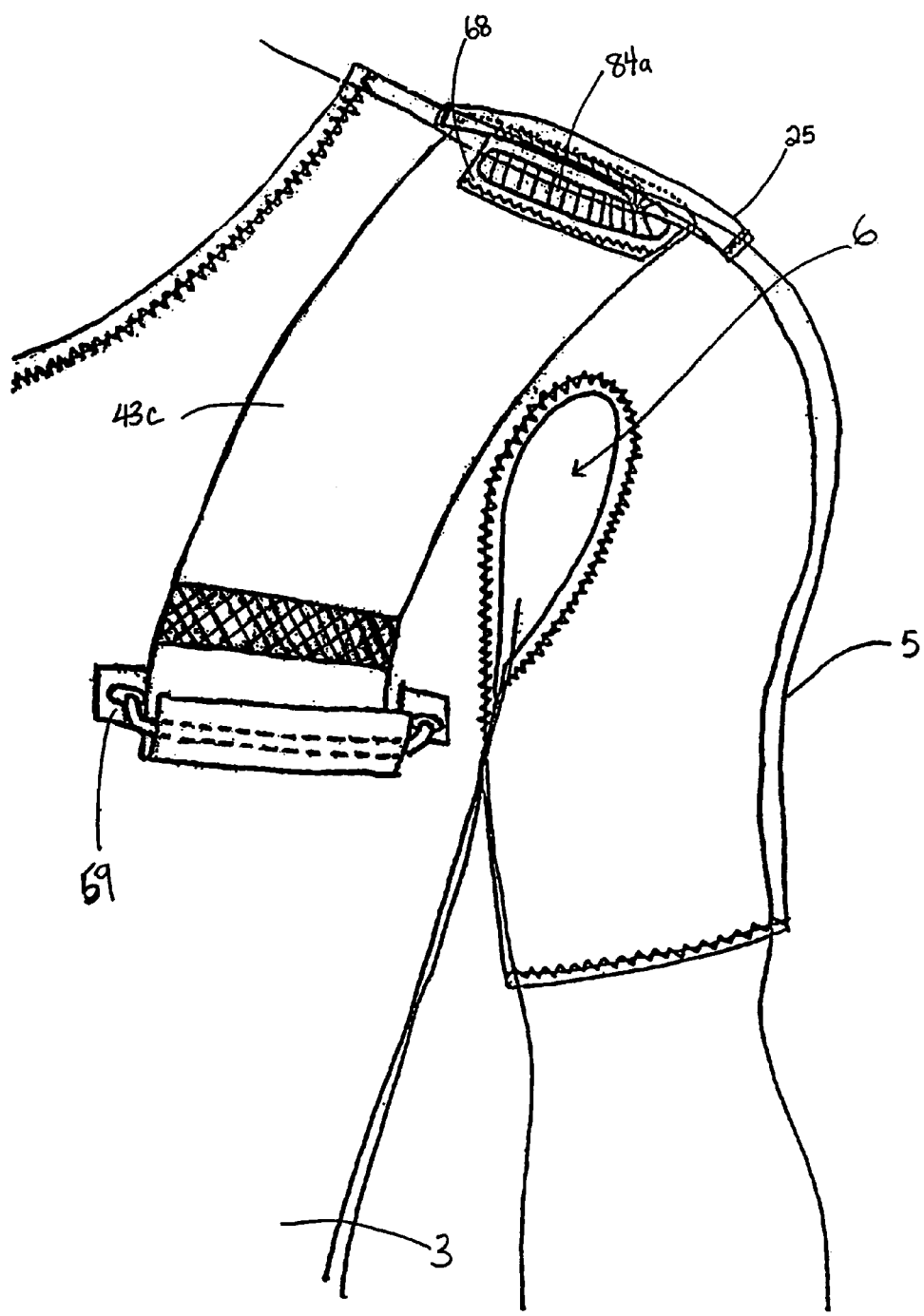
FIG. 11 is a front view of a shoulder to chest control strap according to yet a further preferred embodiment of the present invention.
Figure 12:
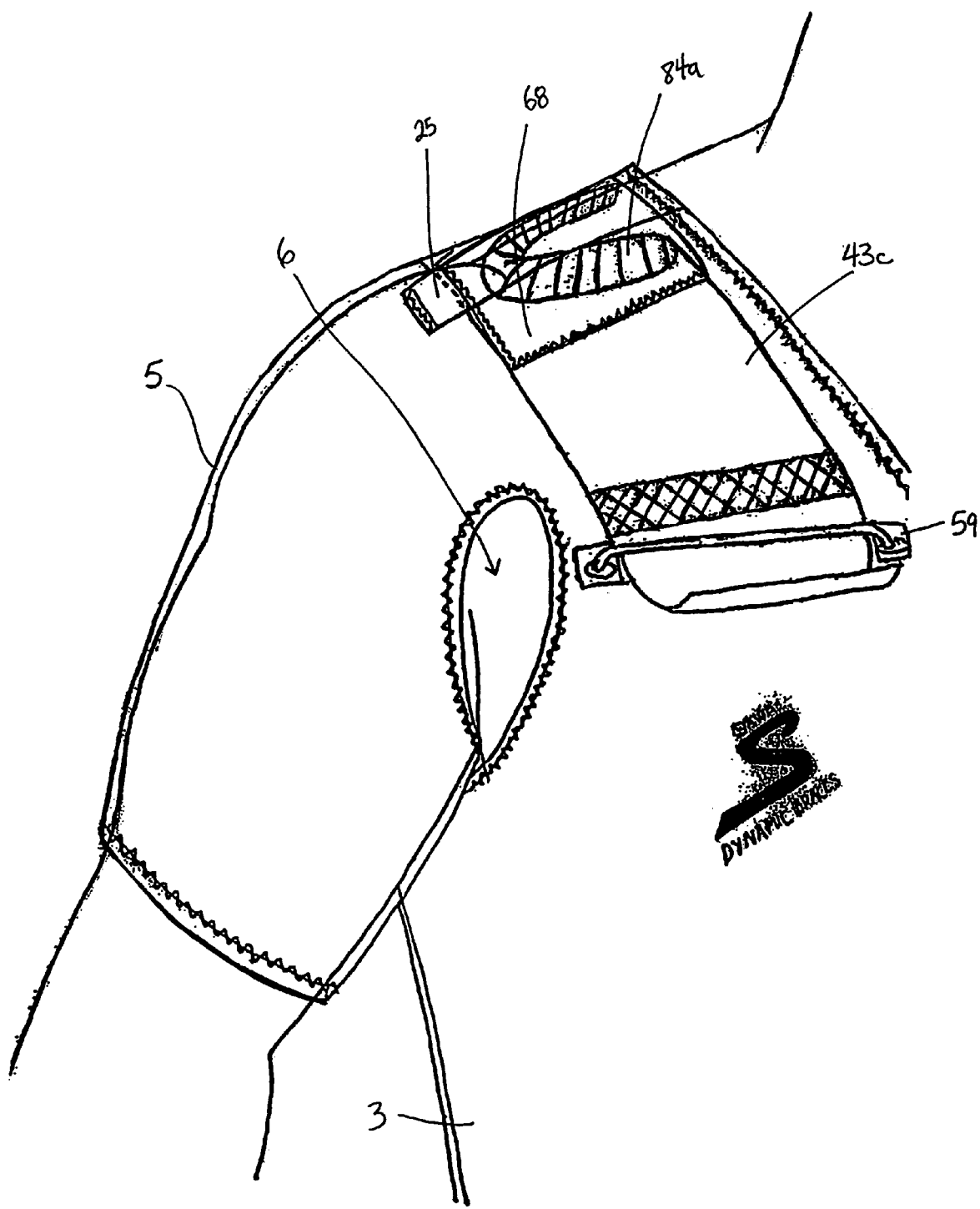
FIG. 12 is a front view of a shoulder to chest control strap slightly modified from that shown in FIG. 11.

In an alternate embodiment as illustrated in FIGS. 11 and 12, the control strap 43c extends from the chest region of the torso fitting part 3 to a location on the rear of the torso fitting part 3. In this embodiment, control strap 43c is anchored to a strap mounting location on the chest portion of the torso fitting part 3. The first strap end region and second strap end region of control strap 43c are anchored to adjustment anchors 59 permanently affixed to the torso fitting part 3. The strap end region of the control strap 43c is threaded through the adjustment anchor 59, and is folded back over adjustment anchor 59 to form a loop part, wherein the interlocking Velcro™ surface region 51 secures the strap end region to the adjustment anchor 59.

Figure 14:
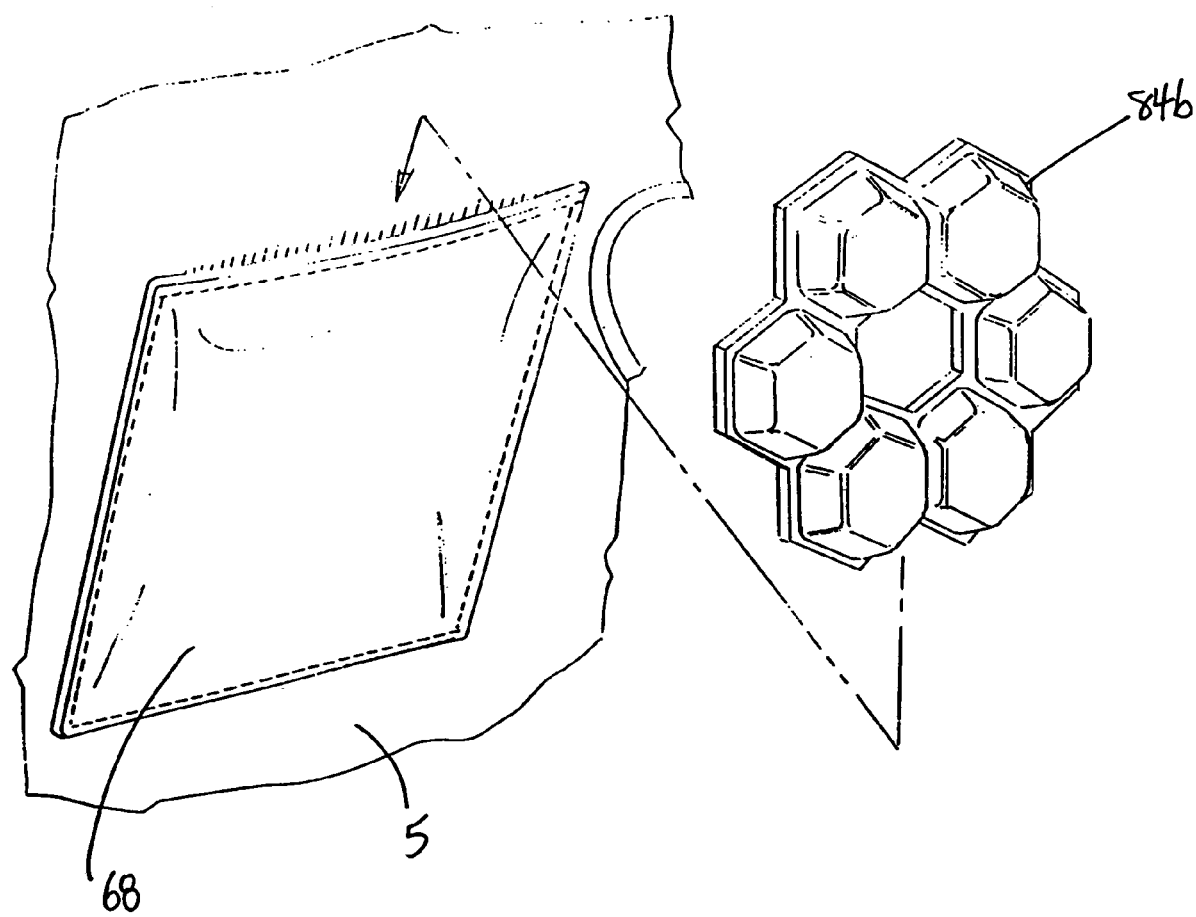
FIG. 14 is a perspective view of the pad of FIG. 13 to be fitted to the underside of a shoulder complex system.
Figure 15:
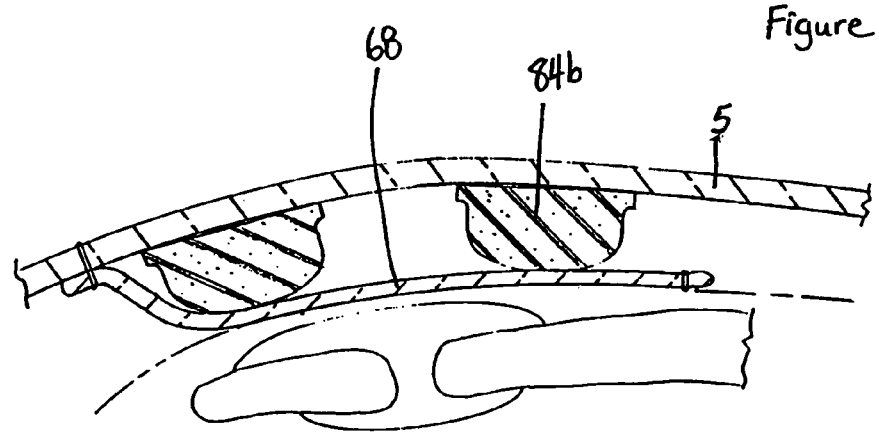
FIG. 15 shows the pad of FIG. 14 in position in the shoulder complex control system and seated atop the shoulder complex.

Furthermore, to avoid undue pressure on the injured shoulder joint as a result of the force and tension of the control strap 43c, a high density pad 84 is removeably positioned beneath control strap 43c over the acromioclavicular joint, to be described later in detail. To ensure the correct positioning of the pad 84, a pad insertion pocket 68 is utilized for removeably receiving a pad 84. The pad insertion pocket 68 is preferably positioned over the acromioclavicular joint, as illustrated in FIGS. 14 and 15.

Control strap 43d is provided to allow further adjustments of the torso fitting part 3 to accommodate different torso widths. Control strap 43d permits the tightening of the lower part of the torso fitting part 3 to increase the fit of the torso fitting part 3 and to prevent the torso fitting part 3 from rising up. The first strap end region 45 of control strap 43c is threaded through buckle 17, and is folded back over buckle 17 to form a first loop part 49. The first loop part 49 includes an interlocking Velcro™ surface region 51 to secure the first strap end region 45 to buckle 17. The second strap end region 53 is preferably permanently secured to the torso fitting part 3.

It can also be appreciated that the number of control straps used in the system 1 can be customized to accommodate the specific injuries and needs of the user. When all the control straps 43 as illustrated in FIGS. 1 and 2 are used, the system 1 can restrict and limit posterior and anterior movement of the shoulder, as well as multidirectional movement of the shoulder.

It can be appreciated that by adjusting the first loop part 49 and/or the second loop part 53 of control straps 43, the length of each control strap is independently adjusted. The adjustments are easily and simply done. The adjustability of the control straps allows the user to selectively customize the range of movement of the shoulder. Thus, the adjustability of the control straps 43 allows the shoulder complex and upper arm injury reduction system 1 to be used throughout the duration of rehabilitation, as a wide range of motions can be achieved: from holding the shoulder completely immobile to allowing motion of the shoulder in limited specific directions. The degree of mobility of the system 1 can be adjusted to accommodate the regained mobility of the user's shoulder.

Figure 7:
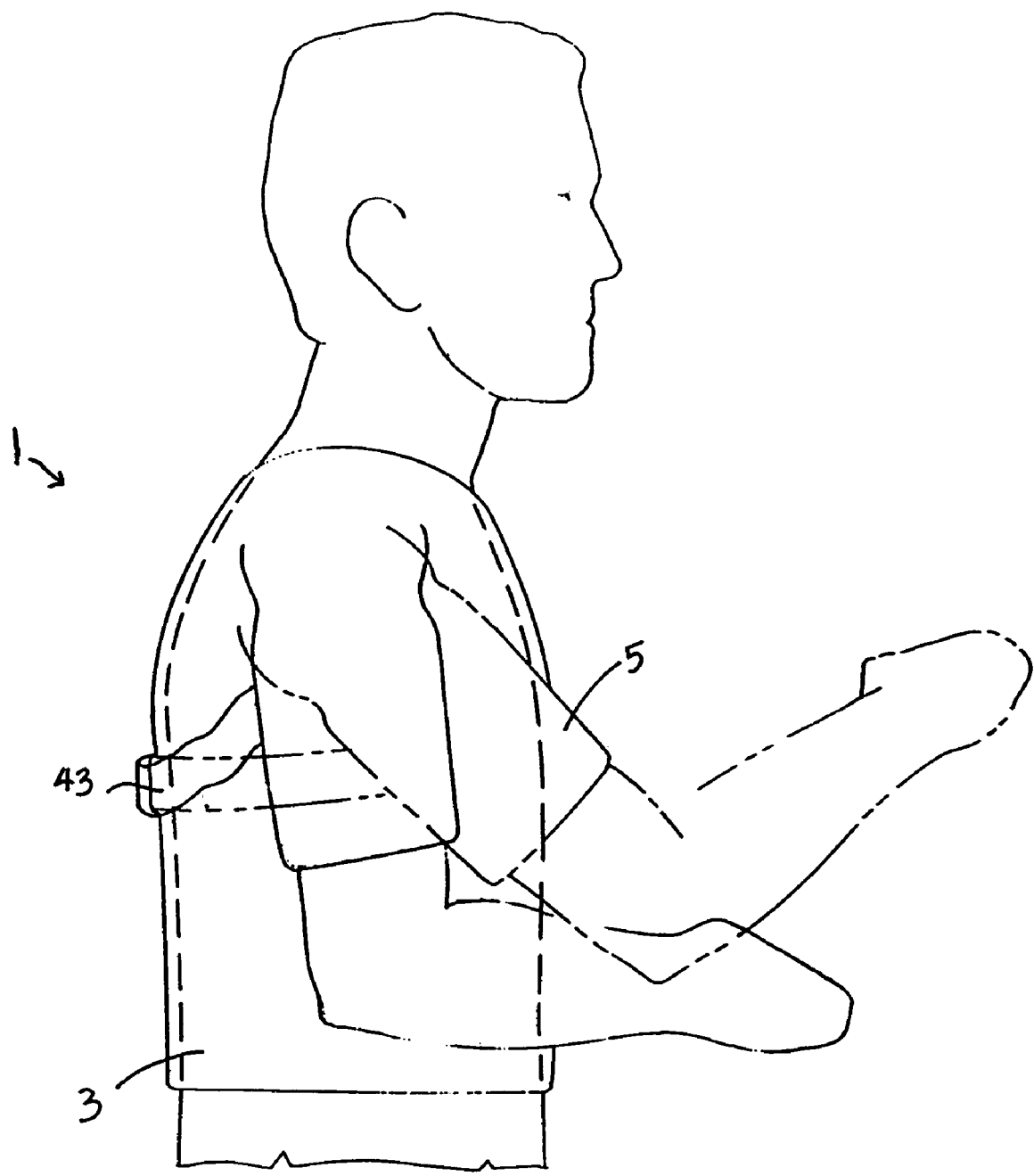
FIG. 7 is a side view of an individual using the system of the present invention and showing various different ranges of motion to which the system can be set.

FIGS. 3, 4, and 7 further demonstrate the principals of the invention. Within the permitted range of motion as set by the length of the control straps 43, there is complete mobility of the arm and shoulder region. However, movement of the arm and shoulder beyond the length of the control straps 43 is prevented by the inelastic material of the straps.

Figure 5:
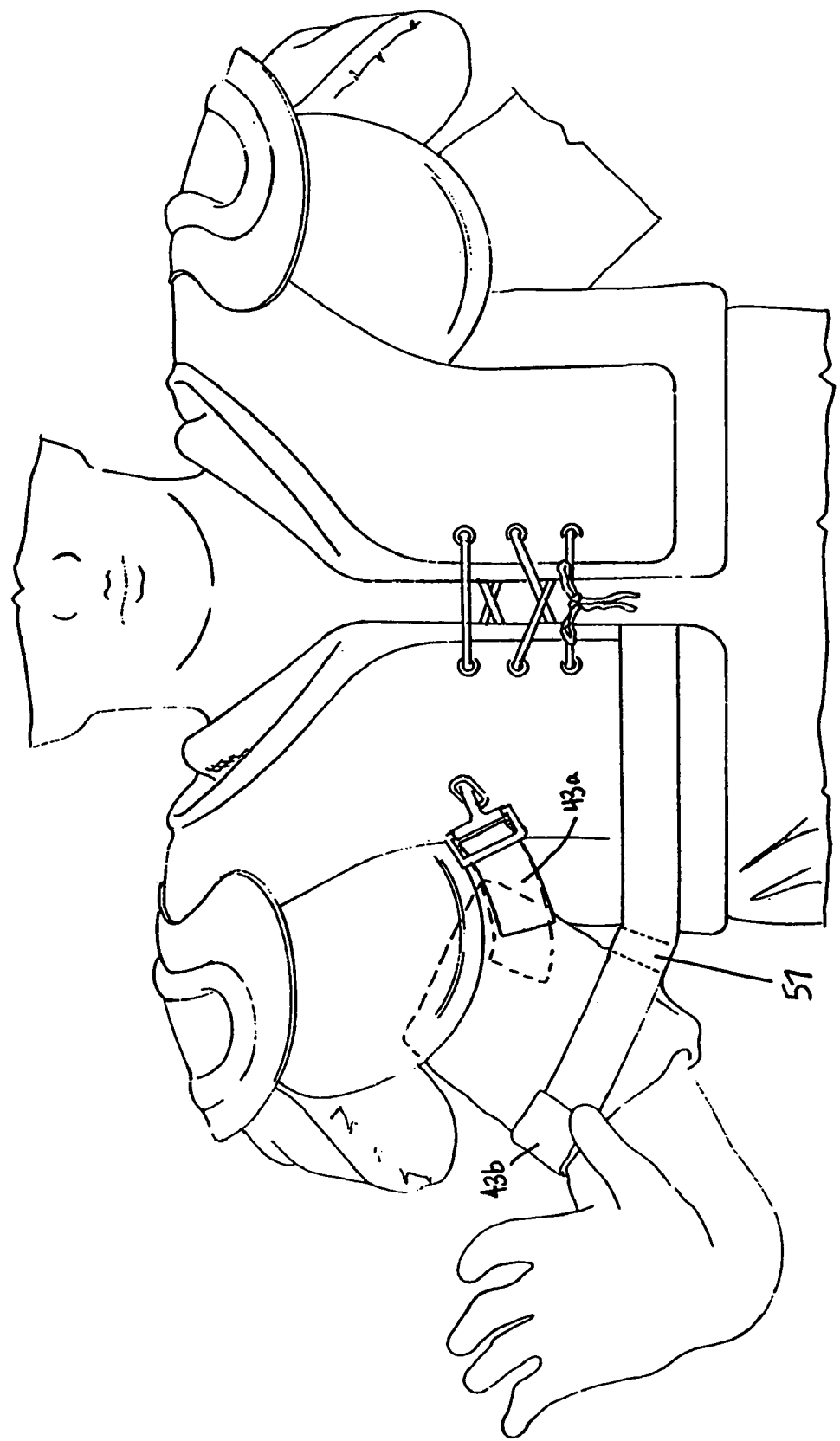
FIG. 5 is a front view of a set of shoulder pads modified to incorporate the system of the present invention.
Figure 6:
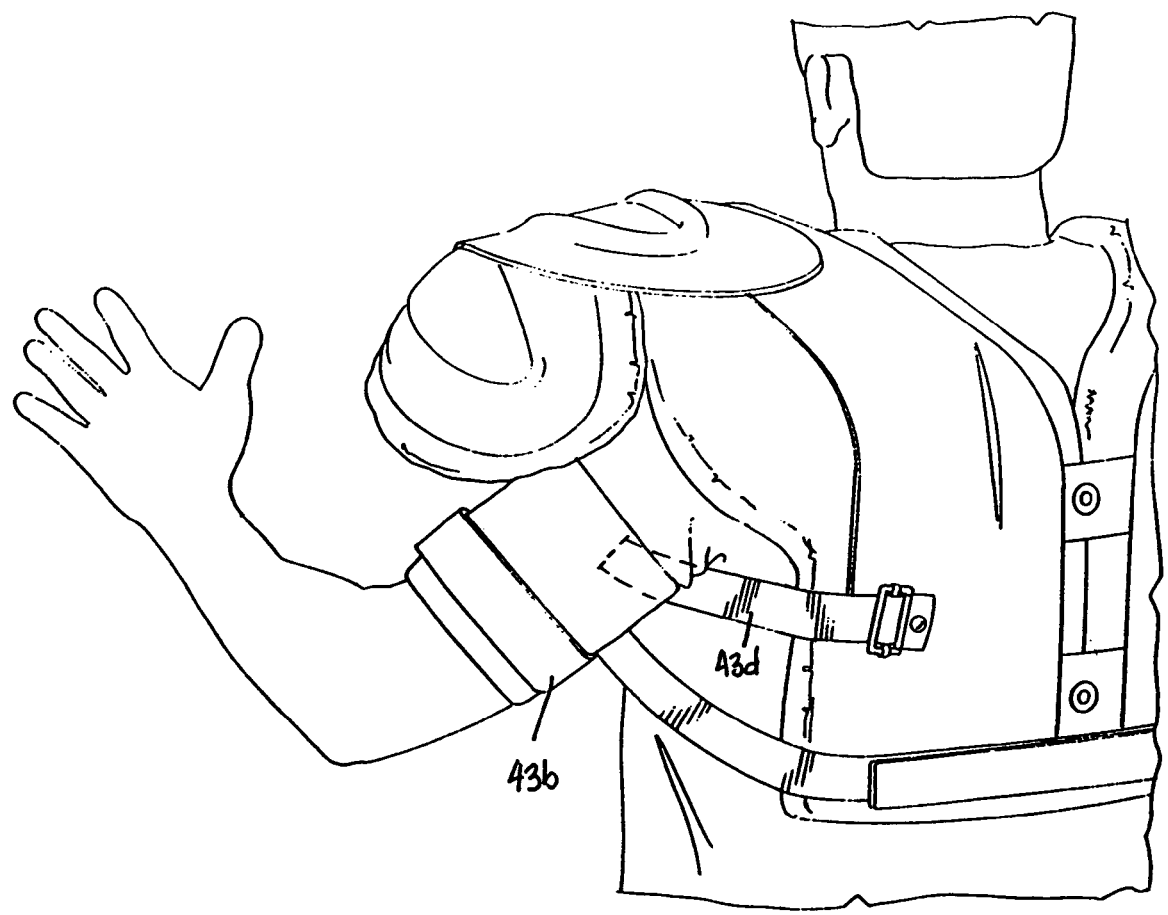
FIG. 6 is a rear perspective view of the shoulder pads of FIG. 5 using a rear control strap.

It can be appreciated that the principals of the invention can be used to modify existing athletic equipment to accommodate injured athletes. In particular, this is useful because athletes will not be required to wear a separate brace beneath their equipment. As illustrated in FIGS. 5 and 6, the principles of the shoulder complex and upper arm injury reduction system 1 is incorporated into an athletic shoulder pad. Control straps 43 are anchored or fixed directly to the shoulder pads at one end, and adjustments to the length of the control strap is made at the other end. However, this example is not limiting and other athletic equipment can be modified and are considered within the scope of the invention.

Figure 9:
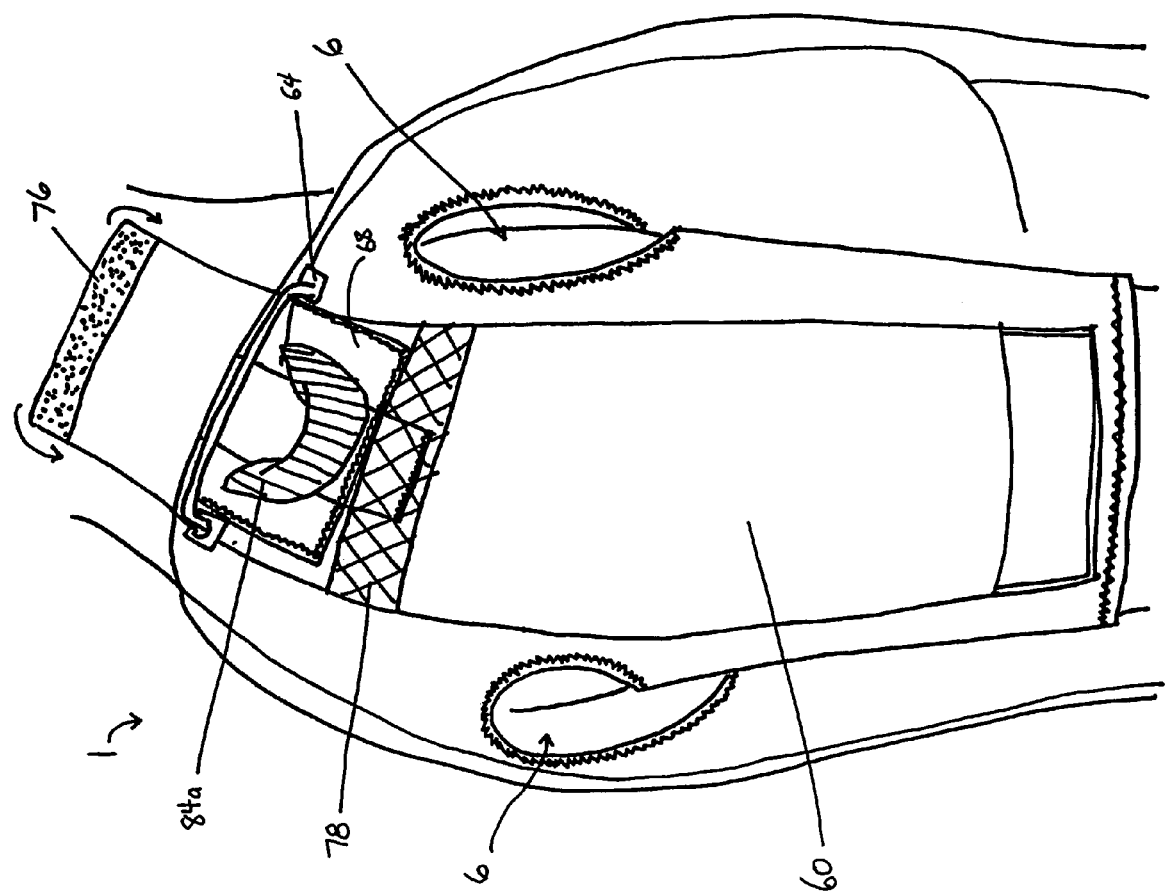
FIG. 9 is a side view of a traction control system for producing traction between the shoulder and the upper arm according to a further preferred embodiment of the present invention.
Figure 10:
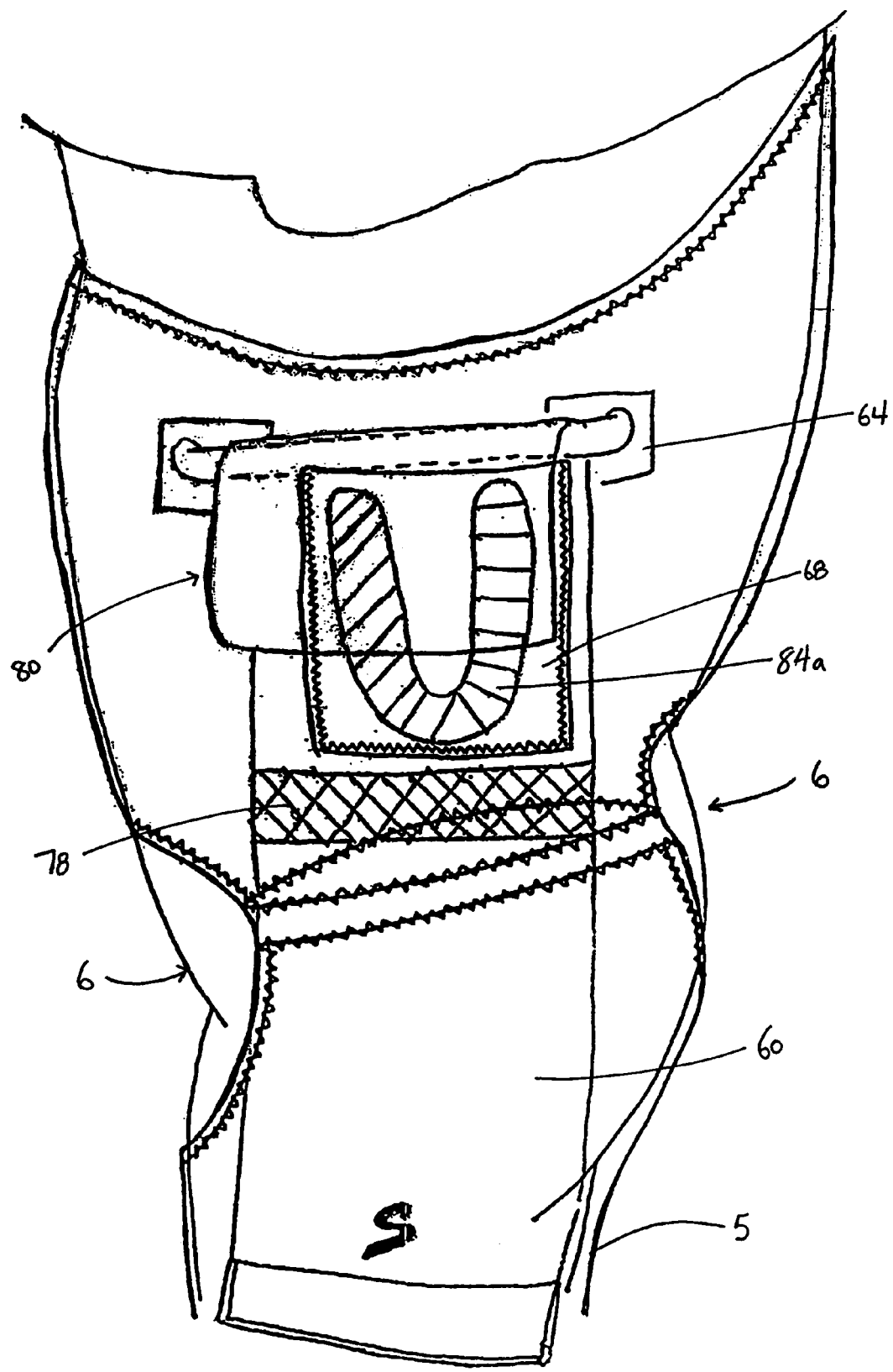
FIG. 10 is a top perspective view looking down on a shoulder and upper arm traction control system slightly modified from that shown in FIG. 9.

In a further aspect of the invention, the shoulder complex and upper arm injury reduction system 1 includes a control strap 60. In this embodiment, as illustrated in FIGS. 9 and 10, it is preferable that the upper arm wrap part 5 fit snugly around the upper arm region. The first surface of control strap 60 comprises at least one interlocking Velcro™ surface region to secure traction strap 60 to Velcro™ surface member 22 on upper arm wrap part 5. The upper arm wrap part 5 further comprises an adjustment anchor 64, and a pad insertion pocket 68. Control strap 60 further comprises an end region with a Velcro™ surface region 76.

Control strap 60 is preferably made from an inelastic non-stretch material, such as woven nylon. Control strap 60 is preferably comprised of a single piece of material, however, it can be appreciated that control strap 60 can be comprised of at least one interconnecting pieces of material.

The end region of the control strap 60 is threaded through the adjustment anchor 64, and is folded back over adjustment anchor 64 to form a loop part 80 wherein the Velcro™ surface region 76 attaches to a Velcro™ receiving region 78. The control strap 60 provides traction and upward lift of the arm so as to approximate the humerus and glenoid labrum and capsule of gleno-humeral. Controlling the level of traction can be controlled through the adjustment of control strap 60.

As illustrated in FIGS. 9 and 10, the adjustment anchor 64 is mounted at a location on the shoulder capping region. However, it is recognized that the adjustment anchor 64 can also be mounted at a location below the shoulder capping region.

As illustrated in FIGS. 14 and 15, to avoid undue pressure on the injured shoulder joint as a result of the force and tension of the control strap 60 or control strap 43c, a pad 84 is removeably placed in the pad insertion pocket 68, wherein the pad insertion pocket 68 and the pad 84 are located directly over the acromioclavicular joint. Pad 84 is preferably made from a high density material to allow the pad to absorb the force created by the control strap.

Figure 13:
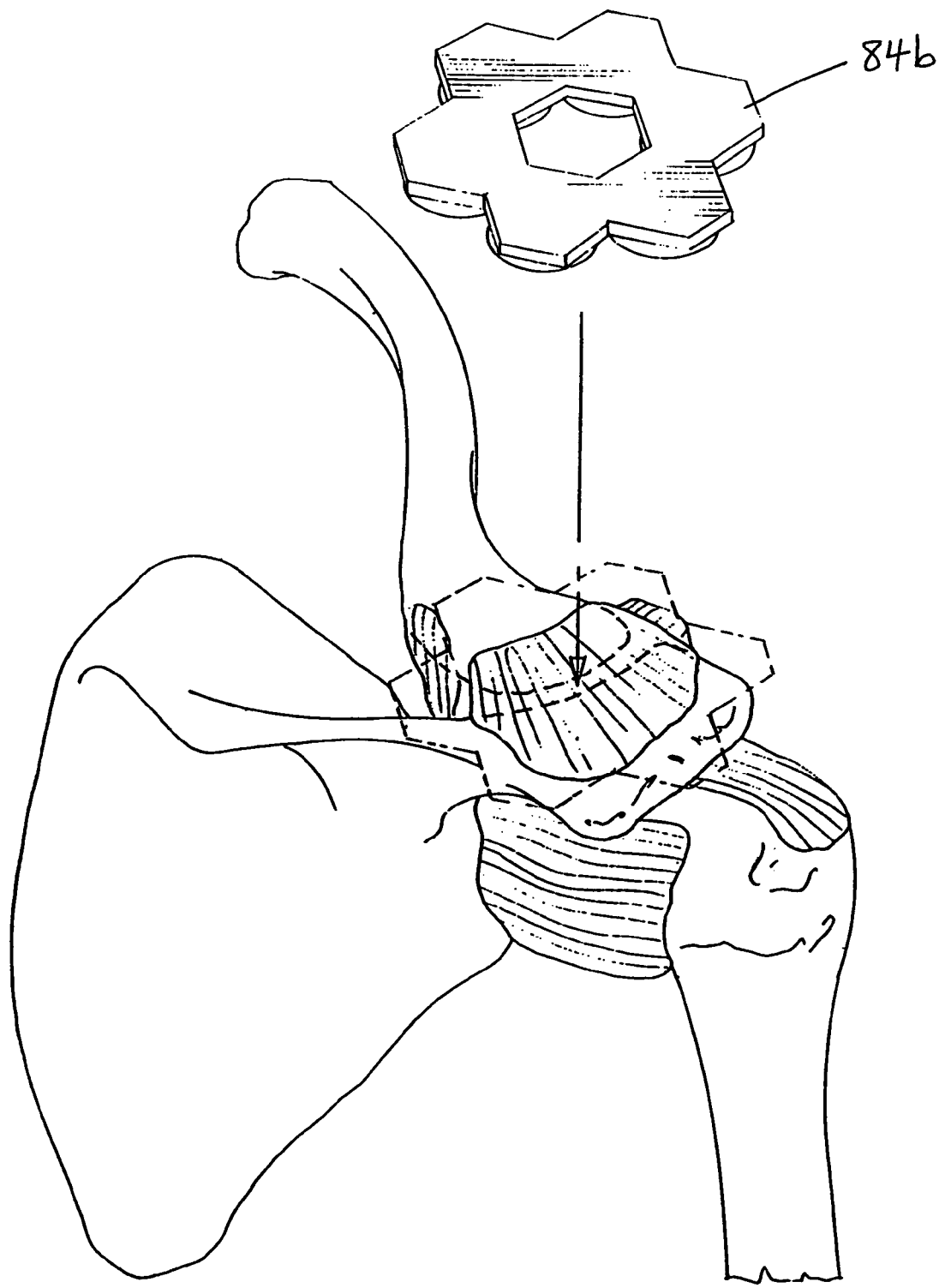
FIG. 13 is a perspective view of a shoulder complex and a pad exploded from a control system according to a preferred embodiment of the invention for fitting with the shoulder complex.

As illustrated in FIG. 13, to avoid undue direct pressure on the acromioclavicular joint, the pad 84 is shaped to avoid direct contact with the acromioclavicular joint and to contact the area immediately surrounding the acromioclavicular joint. It can be appreciated that the pad 84 can be provided in a variety of shapes, and the pad 84 is preferably shaped in a C-shape 84*a*, or in a ring of hexagons 84*b*.

Although the invention has been described with respect to specific preferred embodiments, it should be appreciated that other embodiments utilizing the concept of the present invention are possible without departing from the scope of the invention. The invention is not intended to be limited to the specific embodiments.

The embodiments of the invention in which an exclusive property or privilege is claimed are defined as follows:

1. A shoulder complex and upper arm injury reduction system comprising:
    a torso fitting part,
    an upper arm wrap part having an exterior surface provided with a movement control strap coupling region extending at least substantially around said upper arm wrap part, and
    at least one movement control strap, having at least one torso attachment region for attachment to at least one strap anchor on the torso fitting part wherein said torso attachment region includes a first loop forming part which loops through and secures with said at least one strap anchor to secure the torso attachment region with the torso fitting part, and
        having an interlocking strap region which interlocks with the movement control strap coupling region of the upper arm wrap part to provide interlocked wrapping of said interlocking strap region around said upper arm wrap part,
    wherein said at least one movement control strap is adjustable to different strap lengths between said torso attachment region and said interlocking strap region, said at least one movement control strap being made from an essentially inelastic material such that said at least one movement control strap controls separation and rotation of said upper arm wrap part relative to said torso fitting part beyond any one of the strap lengths to which said at least one movement control strap is adjusted.

2. A system as claimed in claim 1 wherein said first loop forming parts include interlocking VELCRO surfaces and is adjustable to different loop formations to provide the different strap lengths to which said movement control strap is adjusted.

3. A system as claimed in claim 1, wherein a first strap anchor is provided to a front side of said torso fitting part, said movement control strap extending across said front side of said torso fitting part to said upper arm wrap part to limit rearward movement of said upper arm wrap part relative to said torso fitting part.

4. A system as claimed in claim 1, wherein a first strap anchor is provided to a rear side of said torso fitting part and said movement control strap extends across said rear side of said torso fitting part of said upper arm wrap part to limit forward movement of said upper arm wrap part relative to said torso fitting part.

5. A system as claimed in claim 1, wherein said system comprises
    one movement control strap having a first torso attachment region at a first strap end region, a second torso attachment region at a second strap end region, and the interlocking strap region positioned between said first and second end regions,
    a first strap anchor provided to a front side of said torso fitting part, said movement control strap extending across said front side of said torso fitting part to said upper arm wrap part to limit rearward movement of said upper arm wrap part relative to said torso fitting part,
    a second strap anchor provided to a rear side of said torso fitting part and said movement control strap extends across said rear side of said torso fitting part of said upper arm wrap part to limit forward movement of said upper arm wrap part relative to said torso fitting part.

6. A system as claimed in claim 1, wherein said system comprises:
    a first movement control strap having one torso attachment region at a first strap end region, and the interlocking strap region positioned at a second strap end region,
    a second movement control strap having one torso attachment region at a first strap end region, and the interlocking strap region positioned at a second strap end region,
    a first strap anchor provided to a front side of said torso fitting part, said first movement control strap extending across said front side of said torso fitting part to said upper arm wrap part,
    a second strap anchor provided to a rear side of said torso fitting part and said second movement control strap extends across said rear side of said torso fitting part of said upper arm wrap part,
    wherein said first movement control strap and said second movement control strap extending across said front and rear surfaces of said torso fitting part to said first and second strap anchors on said torso fitting part to limit both forward and rearward movement of said upper arm wrap part relative to said torso fitting part.

7. A system as claimed in claim 1,
    wherein the torso fitting part comprises a shoulder capping region, and the system further comprising:
    a plurality of control straps having a first strap region which is anchored at the torso fitting part and having a second strap region which is anchored at the upper arm wrap part, said control straps being adjustable to different strap lengths between said first and second strap regions, said strap being made from an essentially inelastic material such that said strap prevents separation of said upper arm wrap part from said torso fitting part beyond any one of the strap lengths to which said strap is adjusted, and
    a traction control strap extending from the shoulder capping region to a strap mounting location within said system below the shoulder capping region, the traction control strap being length adjustable to place tension on and to produce traction within said system between the shoulder capping region and the strap mounting location below the shoulder capping region.

8. A system as claimed in claim 1 wherein said movement control strap coupling region of the upper arm wrap part is a first VELCRO surface and wherein said interlocking strap region includes a second VELCRO surface which interlocks with said first VELCRO surface.

9. A system as claimed in claim 5, wherein the movement control strap is interconnected at a position between the interlocking strap region and the strap ends.

10. A system as claimed in claim 6, wherein the first and second movement control straps are interconnected at a position between the first and second strap end regions.

11. A shoulder complex and upper arm injury reduction system comprising:
- a torso fitting part, having a shoulder capping region and a plurality of strap anchors,
- an upper arm wrap part, having an exterior surface provided with a movement control strap coupling region extending at least substantially around the upper arm wrap part,
- a movement control strap having
  - a first torso attachment region at a first strap end region,
  - a second torso attachment region at a second strap end region, and
  - an interlocking strap region positioned between said first and second end regions, said interlocking strap region interlocks with the movement control strap coupling region of the upper arm wrap part to provide interlocked wrapping of said interlocking strap region around said upper arm wrap part,
  - wherein said first torso attachment region includes a first loop forming part which loops through and secures with a first strap anchor provided to a front side of said torso fitting part, said movement control strap extending across said front side of said torso fitting part to said upper arm wrap part, and said second torso attachment region includes a first loop forming part which loops through and secures with a second strap anchor provided to a rear side of said torso fitting part and said movement control strap extending across said rear side of said torso fitting part to said upper arm wrap part, to limit forward and rearward movement of said upper arm wrap part relative to said torso fitting part,
- a plurality of control straps having a first strap region anchored at the torso fitting part and having a second strap region which is anchored at the upper arm wrap part, said control straps being adjustable to different strap lengths between said first and second strap regions,
  - said control straps being made from an essentially inelastic material to prevent separation of said upper arm wrap from said torso fitting part beyond said strap lengths,
- a traction control strap extending from the shoulder capping region to a strap mounting location within said system below the shoulder capping region, the traction control strap being length adjustable to place tension on and to produce traction within said system between the shoulder capping region and the strap mounting location, below the shoulder capping region, and
- a foamed pad beneath said traction control strap at said shoulder capping region.

* * * * *